United States Patent [19]

Weston

[11] Patent Number: 5,217,470

[45] Date of Patent: Jun. 8, 1993

[54] APPARATUSES AND METHODS FOR FORMATION AND USE OF A SLIPKNOT AS A SURGICAL SUTURE KNOT

[76] Inventor: Peter V. Weston, 705 Oak Hills Medical Bldg., 7711 Louis Pasteur Dr., San Antonio, Tex. 78229

[21] Appl. No.: 693,943

[22] Filed: Apr. 29, 1991

[51] Int. Cl.$^5$ .............................................. A61B 17/00
[52] U.S. Cl. ........................................ 606/148; 606/1; 289/1.2; 289/1.5; 289/2; 289/17
[58] Field of Search .................. 289/15, 13, 12, 2, 1.5, 289/17, 18; 66/1 A, 4; 606/224, 139, 145, 144, 148, 228

[56] References Cited

U.S. PATENT DOCUMENTS

| | | | |
|---|---|---|---|
| 2,134,066 | 10/1938 | Van Ness | 66/4 |
| 3,625,556 | 10/1969 | Stromberg | 289/17 |
| 3,717,012 | 2/1973 | Misner et al. | 66/1 A |
| 4,204,542 | 5/1980 | Bokros et al. | 606/224 |

OTHER PUBLICATIONS

Brainard, F. R., *Knots, Splices, Hitches, Bends, and Lashings*, Practical Publishing Co., N.Y., 1893, pp. 9 and 12.
Graumont, R. and Hensel, J., *Encyclopedia of Knots and Fancy Ropework*, Cornell Maritime Press, N.Y., 1945, pp. 12-13 and 19-21.

*Primary Examiner*—Stephen C. Pellegrino
*Assistant Examiner*—Jeffrey A. Schmidt
*Attorney, Agent, or Firm*—David G. Henry

[57] ABSTRACT

Disclosed is a novel use of the capstan knot as a suture knot in surgical procedures along with a simplified method for such knot's formation, an apparatus for forming a protoknot of the capstan knot, and a preformed suture system which provides a capstan knot protoknot mounted on a knot tightener having a channel passing therethrough. The protoknot, once formed, is transformed into a completed capstan knot by straight-line passage of the standing part of the filament, to which a surgical needle is initially attached, through a defined path through the protoknot after passage of the filament through the patient's tissue.

13 Claims, 14 Drawing Sheets

APPARATUSES AND METHODS FOR FORMATION AND USE OF A SLIPKNOT AS A SURGICAL SUTURE KNOT

REFERENCE TO OTHER PATENT APPLICATIONS BY APPLICANT HEREIN

Another patent application (no serial number yet received) was filed by Applicant herein on Apr. 9, 1991. The "Weston Knot" referred to herein is the knot likewise denoted in such co-pending application.

BACKGROUND OF THE INVENTION

1. Field of The Invention

Applicant's invention relates to knots such as are used as suture knots in surgical procedures.

2. Background Information

Most (but not all) knots preferably exhibit the characteristic of not slipping or becoming untied during their normally anticipated use(s). The principle feature of a knot which is least likely to slip or unintentionally become untied is that of having more rather than fewer distortions of the filament which forms the knot within the bounds of the knot.

In the case of a slipknot, one segment of the filament which extends from the knot's free loop, through the body of the knot and to and including the terminus of the filament is referred to as the "standing part." For slipknots then, the more forced bends in the standing part as necessitated by the knot design, the more resistant to slippage and becoming untied the knot in its tightened state tends to be.

In the surgical field, suture knots most certainly should not ordinarily slip nor become untied under any circumstances. It is to knots to be used as sutures in surgical procedures to which Applicant's invention principally relates.

Presently, most suture knots used in surgical procedures are tied completely by hand or, in instances where the fingers cannot reach, using surgical instruments Certain apparatuses have been proposed which assist in forming suture knots. However, the prior apparatuses and associated methods of use provide assistance only in tying relatively simple knots or only small portions of more complicated knots.

At present, the most common knots used for sutures are the square and the surgeon's knots. The square knot is a simple knot, but difficult to fashion solely with surgical instruments such as are necessary in endoscopic surgical procedures. Once formed, the square not is not outstanding among knots insofar as resistance to becoming untied is concerned.

Impetus for developing improved knots along with practical methods and apparatuses for their formation arises from the relatively new field of endoscopic surgery telescope like instruments through a cannula to a point at which internal tissues are to be incised, excised or stitched (the "surgical site"). Certain instruments involved permit visualization of internal structures while others effectuate the actual surgical procedure(s).

Current applications of endoscopic surgery include:

arthroscopic surgery—this form of surgery involves the introduction of instruments into joints. The most common of such procedures involves the knee joint, while others involve inspection of many other joints; and abdominal surgery—endoscopic abdominal surgery is involved in removing gallbladders and appendices and in performing bowel resections. Gynecologists have been performing endoscopic operations on a regular basis in this country for over twenty years in the form of tubal sterilization procedures. These practitioners also use endoscopic procedures for diagnostic purposes, for freeing up adhesions between various pelvic organs and for correcting conditions leading to infertility. The numerous gynecologic procedures currently performed endoscopically include (1) the use of cautery or laser to destroy abnormal tissue areas, (2) removal of ovarian cysts, (3) removal of certain tumors from the uterus, (4) destruction of pain carrying nerve fibers in patients who have abdominal pain, and (5) procedures requiring knot tying such as bladder suspension operations, hysterectomies and removal of ovaries.

It is anticipated that within the next three to five years 50% of operations that are currently being performed through large abdominal incisions will be performed endoscopically. The advantages of endoscopic surgery are (1) the procedures can be performed on an outpatient, day surgery basis thereby decreasing the cost of prolonged hospitalization and (2) shorter convalescence which allows patients to return to work within a day or two of surgery.

Further advancements and greater utilization of endoscopic procedures is currently hampered by the inability to easily tie knots within the abdominal cavity and other relatively inaccessible involved spaces. Currently, surgery is performed by inserting the needle into a hollow body cavity, passing the needle through the tissues, bringing the needle out to the exterior, manually developing a knot and then locking the knot into position by traction on the end of the apparatus which pulls the thread through a hollow tunnel running the length of a 3 mm nylon tube.

It is anticipated that the inventions disclosed herein will greatly facilitate the tying of extra-corporeal knots (knots being tied outside the body to thereafter be slipped into position). This, in turn, will facilitate and expedite such procedures as: Marshall Marchetti Krantz procedures; uterine suspensions; hysterectomies; appendectomies; and bowel resections. Surgeons required to tie knots at the back of the throat, in the chest cavity, in the placement of heart valves, in brain surgery and in the repair of ligaments (i.e. in arthroscopic surgery) will also be greatly served by the inventions disclosed herein.

It is anticipated that the best mode of practicing all embodiments of Applicant's inventions will involve formation of a protoknot prior to beginning surgery leaving only the passage of one filament element through a specified path for completion of the suture knot. In this manner, the knots will, in all but the rarest of instances, be perfectly formed. This will also allow the surgeon to place sutures more quickly thereby lessening the time that the patient is under anesthesia which has obvious advantages. Absent the complete compliment of Applicant's inventions as disclosed herein, surgeons will be required to use the disclosed knots, if at all, only after the difficult task of tying them completely by hand with the concomitant likelihood of incorrectly forming the knots and thereby increasing the likelihood of slippage.

Prior-issued patents which are known to Applicant and which relate either to surgical knots or to knots in general include the following:

U.S. Pat. No. 2,705,656 issued to Shockey on Apr. 5, 1955 describes a knot tying device for use in mending broken wires as are used in wire sound recorders. The Shockey device constructs a square knot from two loose ends of wire.

U.S. Pat. No. 3,580,256 issued to Wilkinson on May 25, 1971 describes a pre-tied suture and method of suturing that utilizes a pair of butterfly loops in a pre-formed configuration. This pre-tied suture encapsulates the two butterfly loops with a transparent casing and allows the end portions of the suture material to extend from the loops out of the casing. A void remains through the interior of the loops through which one end of the suture material may be passed to finish the formation of the knot. The butterfly loops may then be tightened, the casing forced to disintegrate around it. The knot may then be pulled into a formation that involves a square knot.

U.S. Pat. No. 4,923,461, issued to Caspari on May 8, 1990 discloses a method of suturing for arthroscopic surgery that incorporates a hollow needle and a mechanism whereby suture material may be fed through the hollow needle. Caspari prescribes a series of steps from which a suture knot results.

U.S. Pat. No. 4,602,635, issued to Mulholland on Jul. 29, 1986 discloses a "remote surgical knot tier and method of use" intended for arthroscopic surgery. Mulholland uses a rod-like device through a portion of which extends suture material. Mulholland prescribes a series of steps which ultimately results in the formation of a "square" knot.

U.S. Pat. No. 4,621,640, issued to Mulholland on Nov. 11, 1986, discloses a mechanical needle carrier which is intended to hold and position a surgical needle during arthroscopic surgery. This device is intended to set a stitch at a remote location within the tissue cavity and to then release the needle so that it might be withdrawn from the cavity leaving the suture stitch in place.

U.S. Pat. No. 3,834,395 issued to Santos on Sept. 10, 1974, describes a knot tying instrument which utilizes a pair of elongated rods that face each other and are physically attached to one another in a scissor-like arrangement. The Santos device is designed to tighten a suture knot within in a tissue cavity.

U.S. Pat. No. 2,594,086, issued to Larzelere on Apr. 29, 1952, discloses a surgical instrument designed to tie knots in sutures within body cavities. The Larzelere device is in the nature of an elongated rod with means for engaging two ends of a suture filament so as to direct force appropriately for tightening a square knot.

U.S. Pat. No. 4,711,476, issued to Hansen on Dec. 8, 1987 discloses a knot and various methods for the formation thereof.

Significant limitations relating to previously known apparatuses and methods for the formation of suture knots include: (1) being limited to the formation of simple knots such as the square knot; (2) involving knots which require the manipulation of both ends of a length of suture filament which, accordingly, cannot be substantially tied prior to surgery or merely slipped into place; and (3) requiring multiple manipulations outside of the surgical incision with loops thereby formed being afterwards coaxed toward the suture site.

In addition to the knots and apparatuses disclosed in the above-referenced patents, a knot known as the "Roeder loop" is disclosed by K. Semm in the *Operative Manual for Endoscopic Abdominal Surgery*, Year Book Medical Publishers, Inc., 1987:23-31 which publication will be made available in an information disclosure statement to accompany this application.

SUMMARY OF THE INVENTION

It is an object of the present invention to provide a novel use in surgery for a capstan knot, which capstan knot is known in fields unrelated to surgery, but which use in the surgical field has great utility and is nonobvious.

It is yet another object of the present invention to provide a novel and nonobvious apparatus for fashioning a capstan knot for use in the surgical field as a suture knot.

It is yet another object of the present invention to provide a novel method for formation of a capstan knot which method greatly simplifies such formation.

It is another object of the present invention to provide a novel and nonobvious method for forming a novel suture knot which is in the nature of a slipknot which, in turn, can be formed around an elongate member having a channel passing completely through at least a portion thereof.

It is another object of the present invention to provide a suture system which provides a protoknot of a slipknot which can be formed into a finished suture knot by mere passage of the standing part of the protoknot's filament through a tubular member upon which such protoknot is situated.

It is another object of the present invention to provide a suture knot system which is easy to use and which, upon use, results in the formation of a useful suture knot.

In satisfaction of these and related objectives, Applicant's present invention provides apparatuses and methods for forming a capstan protoknot in a configuration for use in surgical procedures as an easily completed and very efficacious suture knot. Applicant's invention permits its practitioner to utilize a capstan knot as a suture knot, but to avoid the difficulty which attends forming the capstan knot completely by hand. The capstan knot, is known, but its benefits as a suture knot have heretofore remained unrecognized.

The capstan knot exhibits superior characteristics for use as a suture knot as relate to ease of placement and resistance to slippage once in place. The capstan knot is a slipknot which can be easily formed leaving a large loop and thereafter easily advanced along the filament (so as to close the loop). Once in its finally desired position, pulling on the standing part (the "needle end" as hereafter referenced) while equally and oppositely pushing the knot "locks" the knot thereby preventing further movement or slippage.

Absent direct person-to-person instruction and lengthy practice, the capstan knot is somewhat difficult to tie completely by hand. Accordingly, Applicant herein provides a very simple method for forming the capstan knot, which method requires only the suture filament and a tubular member in a readily available form.

Furthermore, Applicant provides a novel apparatus for even simpler, almost fully automated formation of the capstan knot. With slight modification the Weston knot can be tied using the novel apparatus, but it was found to be more convenient to develop the model to manufacture the capstan knot.

Still further, Applicant herein discloses suture systems which provide pre-formed protoknots of the capstan knot in configurations permits rapid completion of sutures during surgical procedures along with knot tighteners (both as part of a suture system and separately) which rapidly and safely tighten and lock a capstan suture knot in place.

All embodiments of Applicant's inventions are drawn toward providing a pre-formed capstan protoknot at a surgical procedure which protoknot becomes the desired suture knot by the simple passage of one end or "standing part" of the suture filament along a specified path through the protoknot. Thereafter the knot is slipped into position and tightened or "locked".

BRIEF DESCRIPTION OF THE DRAWINGS

Applicant's invention may be further understood from a description of the accompanying drawings wherein, unless otherwise specified, like reference numbers are intended to depict like components in the various views.

DETAILED DESCRIPTION OF THE PREFERRED EMBODIMENT

Figure 1:
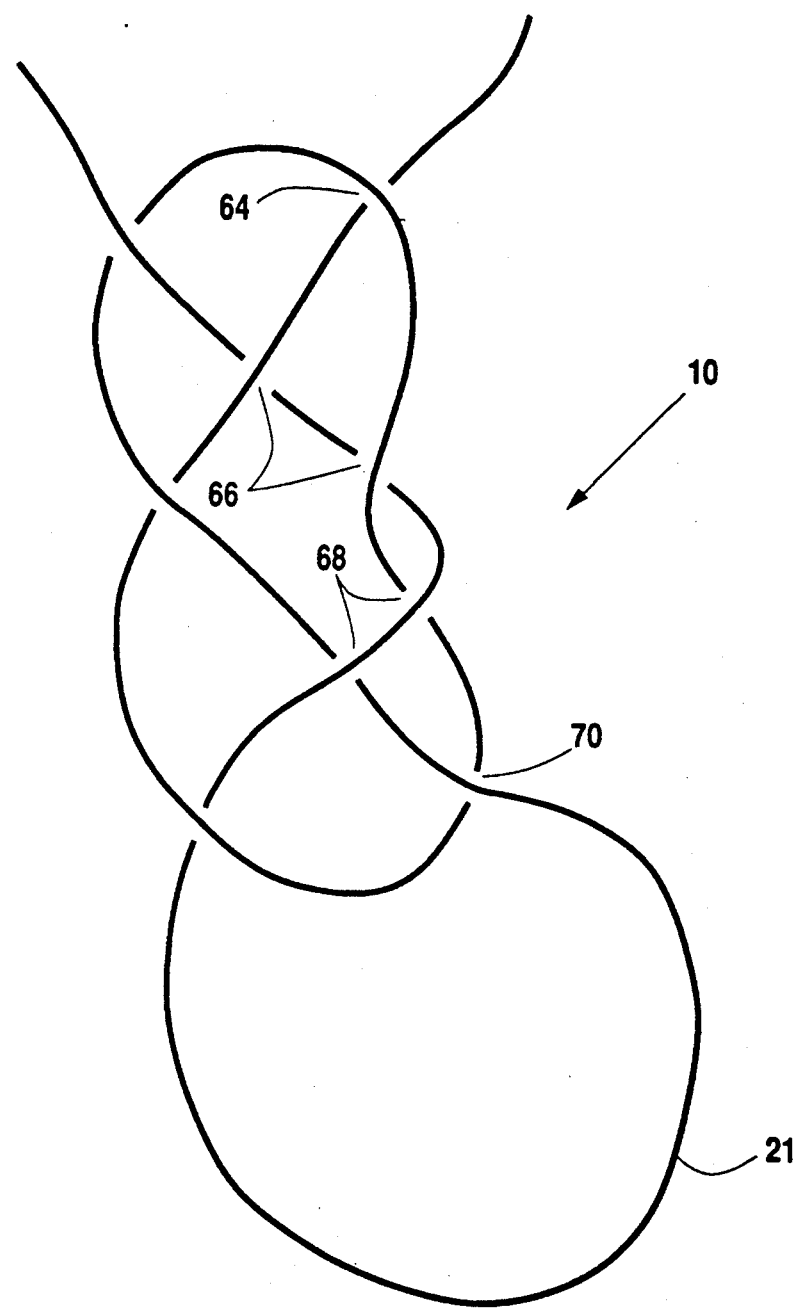
FIG. 1 is an elevational depiction of a loosely formed capstan knot.

A capstan knot 10 is depicted (in loose formation for ease of discernment) in FIG. 1. The capstan knot 10 is a knot which, like the Weston knot, accidentally untied and, therefore, exhibits great utility as a suture knot for use in surgical procedures. The stability of the knot 10 when tightened is due to the distortion of the standing part (filament 21) as it is crossed at locations 64, 66, 68, and 70 as identified in FIG. 1.

The capstan knot 10 is somewhat difficult to teach and to learn. However, providing means by which the capstan knot 10 may be easily formed will accelerate its acceptance and use in surgical procedures. In light of the knot's 10 beneficial characteristics as a suture knot, such acceptance will, in turn, greatly serve all surgical patients.

Accordingly, Applicant herein discloses an apparatus 100, depicted in its entirety in FIGS. 2, 3 and 4 which apparatus 100 mostly automates formation of the capstan knot 10 by forming a capstan protoknot which only requires a single, simple operative step in order to transform it into a completed capstan knot 10 (to be described in more detail later).

In addition, Applicant provides a method for forming the capstan knot 10 using a tube member which is similar to that for forming the Weston knot as described in the above-referenced prior-filed patent application by the present Applicant. Finally, Applicant discloses pre-formed capstan protoknot suture systems which are ready for use in surgical procedures.

Apparatus 100 allows a user to form a capstan knot 10 principally by simply "threading" suture material filament 21 about a defined path and thereafter carrying out rudimentary manipulations of the apparatus 100.

Figure 3:
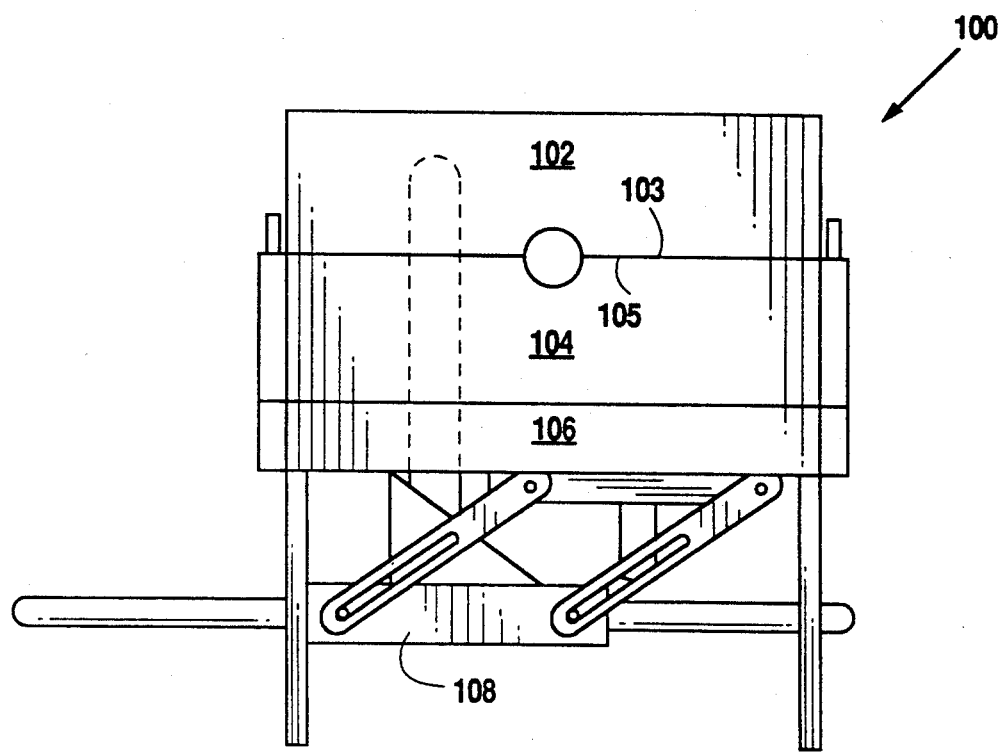
FIG. 3 is a side elevational view of the apparatus depicted in FIG. 2 with the pin sliding plate thereof in one of its two prescribed positions.
Figure 4:
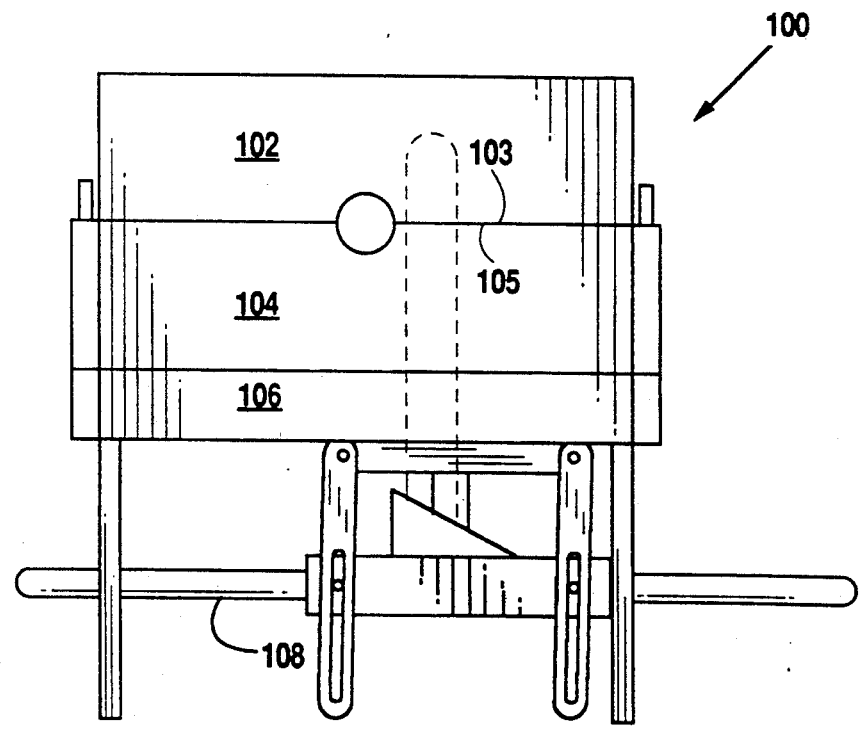
FIG. 4 is a side elevational view of the apparatus depicted in FIG. 2 with the pin sliding plate thereof in one of its two prescribed positions.

Referring principally to FIGS. 3 and 4, apparatus 100 includes four "plates": a front plate 102, a middle plate 104, a pin plate 106 and a pin sliding plate 108. In combination the four plates serve to defined a path for a filament 21 (suture material in the surgical context) and to three-dimensionally position and orient the filament 21 such that the needle end 111 of the filament 21 can pass, by way of a straight "conclusion path", also defined within the apparatus 100, through the bends and loops of the filament 21 as dictated by the defined filament path to thereby complete formation of a capstan knot 10.

Figure 7:
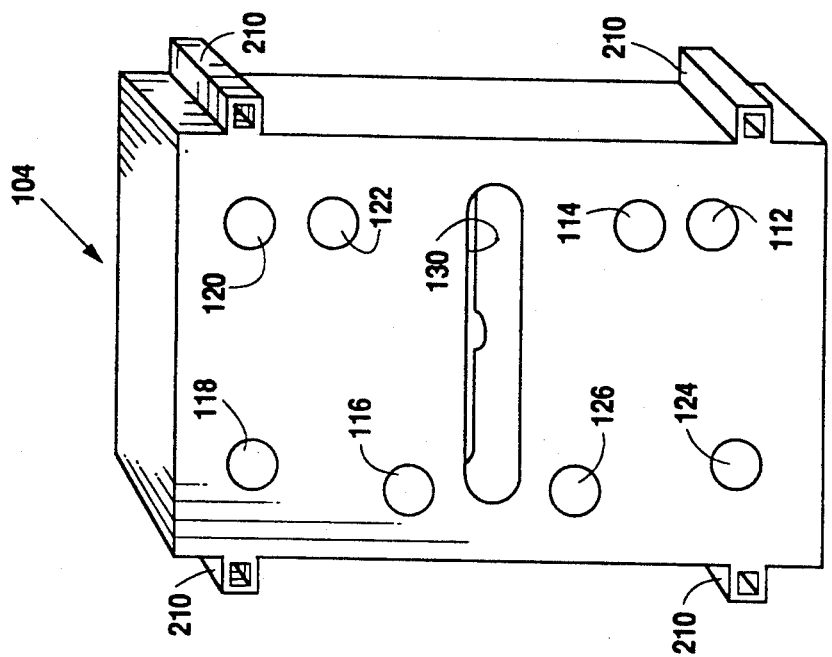
FIG. 7 is a perspective view of the back face of the middle place depicted in FIG. 5.
Figure 6:
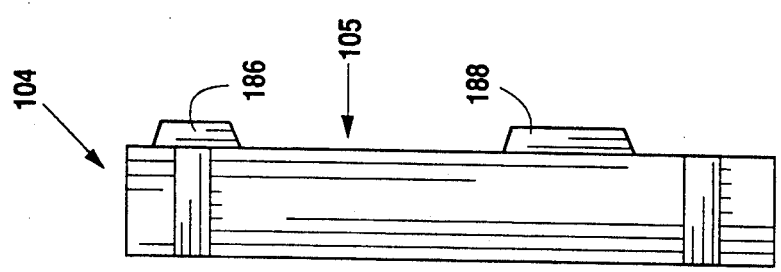
FIG. 6 is an elevational side view of FIG. 5.
Figure 5:
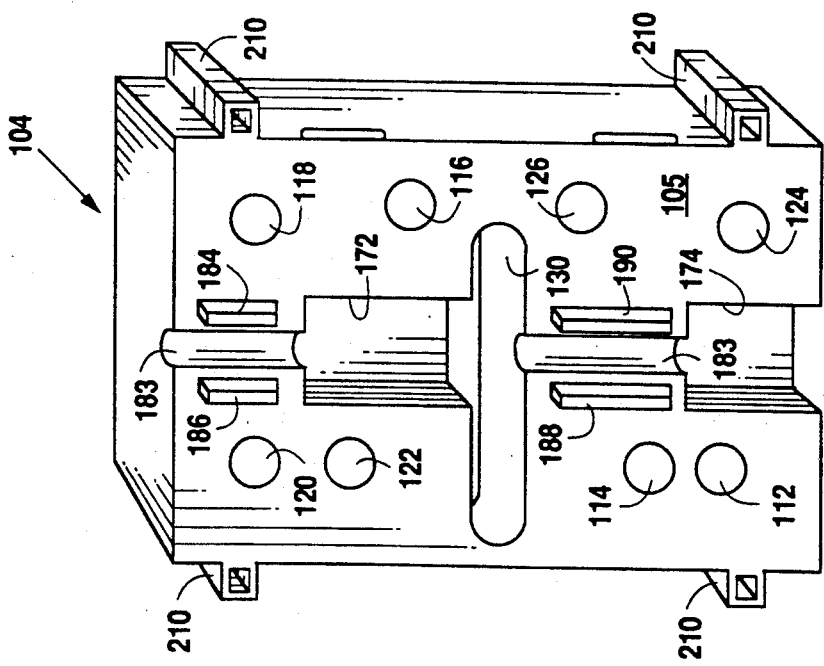
FIG. 5 is a perspective view showing the front face of the middle plate of the apparatus of FIG. 2 and identified by referenced number 105.

FIGS. 5, 6 and 7 depict middle plate 104 with the front face 105 thereof shown in FIG. 5. Middle plate 104 is discussed before the other plates because it serves as the platform on which a filament 21 rests as a user of apparatus 100 threads the filament 21 in forming the protoknot of the capstan knot 10 and is, accordingly, where the protoknot is actually formed. Middle plate 104 exhibits pin holes 112, 114, 116, 118, 120, 122, 124, and 126 which pass completely through middle plate 104. A sliding pin slot 130 also passes completely through middle plate 104. The pin holes 120, 122, 114, 112, 118, 116, 126, and 124 are, respectively, passage routes through middle plate 104 for pins 132, 134, 142, 140, 144, 146, 136, 138 of pin plate 106 (depicted in FIGS. 10 and 11) about and between which a user threads a filament 21 in the initial step of using apparatus 100. The sliding pin slot 130 provides a vertical as well as lateral path for a moving pin 150 of pin sliding plate 108 (depicted in FIGS. 12 and 13), the function of which will be described later.

Figures 8, 9:
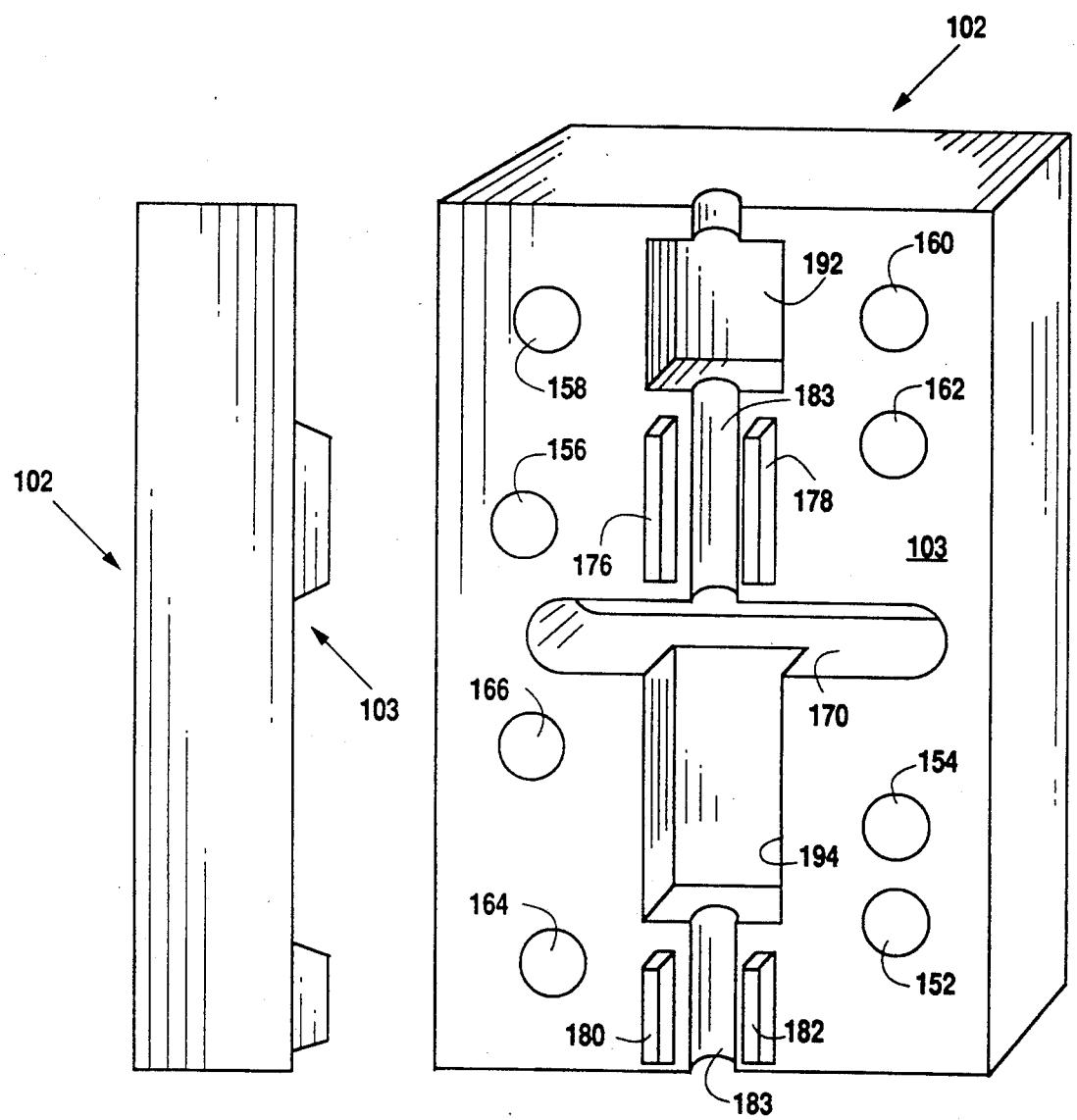
FIG. 8 is an elevational side view of the top plate of the apparatus of FIG. 2.
FIG. 9 is a perspective view of the back face 103 of the top plate of FIG. 8.

Referring to FIGS. 8 and 9, the back face 103 of the front plate 102 exhibits pin holes 160, 162, 154, 152, 158, 156, 166, and 164 respectively into which pins 132, 134, 142, 140, 144, 146, 136, 138 of pin plate 106 extend. In the preferred embodiment, these pin holes pass only partially through front plate 102. Like middle plate 104, front plate 102 also exhibits a slot 170 for accommodating moving pin 150.

Referring in combination to FIGS. 5, 6, 8 and 9, front plate 102 and middle plate 104 dictate a portion of the three-dimensional configuration of a filament 21 which is necessary to permit final formation of capstan knot 10 by simple straight-line passage of the filament's 21 needle end 111 back through its turns and loops (as dictated by the various features of the apparatus 100 as herein described) after the filament 21 is threaded about and between pins 132, 134, 136, 138, 140, 142, 144, and 146 in the hereinafter prescribed manner.

Pins 132, 134, 136, 138, 140, 142, 144, and 146 prescribe the configuration of a filament 21 in that which will be described as the "horizontal plane" for these purposes. Configuration of a filament 21 in the "vertical plane" is dictated by corresponding ridges and recesses on the front face 105 of the middle plate 104 and the back face 103 of the top plate 102.

Front face 105 of the middle plate 104 exhibits two recesses 172 and 174 which respectively correspond to a first pair of ridges 176 and 178 and a second pair of ridges 180 and 182 on the back face 103 of top plate 102. Front face 105 of the middle plate 104 exhibits a first pair of ridges 184 and 186 and a second pair of ridges 188 and 190 which correspond respectively to recesses 192 and 194 on the back face 103 of the top plate 102.

A cylindrical channel is defined between top plate 102 and middle plate 104 by elongate recesses 183 correspondingly positioned on the back face 103 of the top plate 102 and the front face 105 of the middle plate 104. Such channel provides the avenue for the above-referenced "conclusion path".

Figure 10:
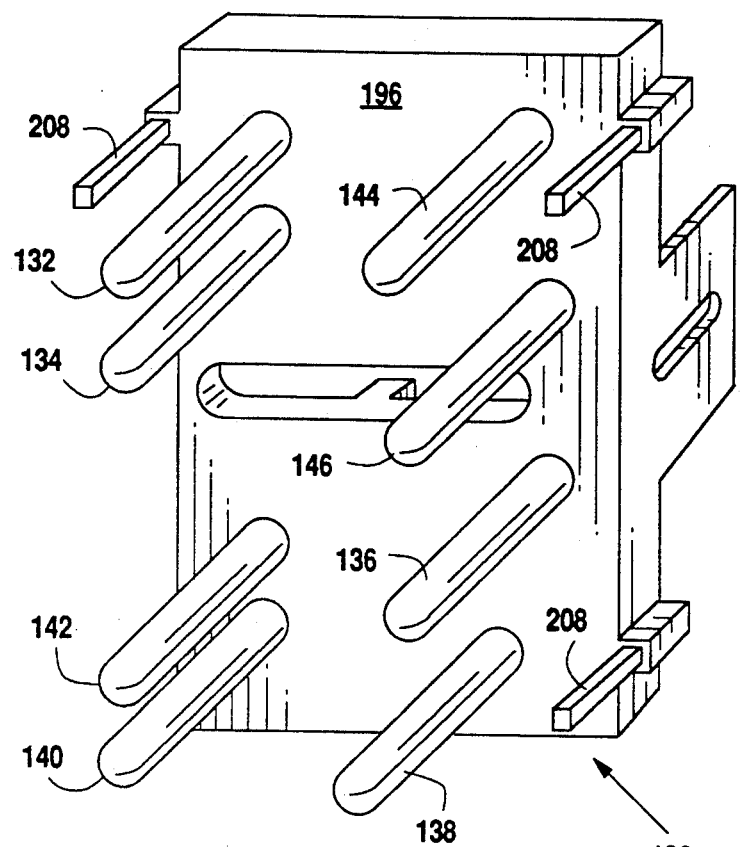
FIG. 10 is a perspective view of the front face of the pin plate of the apparatus of FIG. 2.
Figure 11:
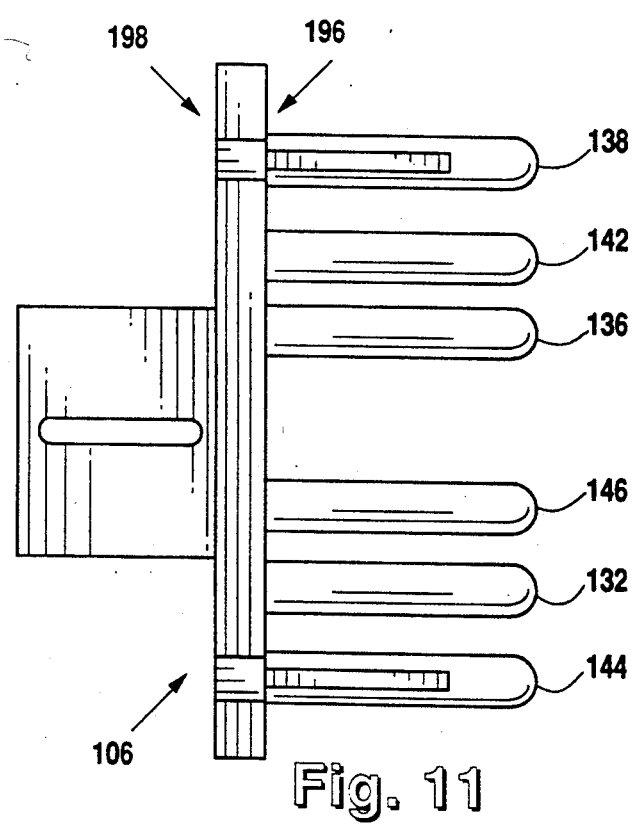
FIG. 11 is a side elevational view of the pin plate of FIG. 10.

Referring to FIGS. 10 and 11, pin plate 106 exhibits eight pins 132, 134, 136, 138, 140, 142, 144, and 146 extending orthogonally from the front face 196 of the pin plate 106. Pins 132, 134, 136, 138, 140, 142, 144, and 146 are positioned on the front face 196 of the pin plate 106 in order to extend respectively through pin holes 120, 122, 126, 124, 112, 114, 118, and 116 of middle plate 104 and pin holes 160, 162, 166, 164, 152, 154, 158, and 156 of front plate 102.

Figure 12:
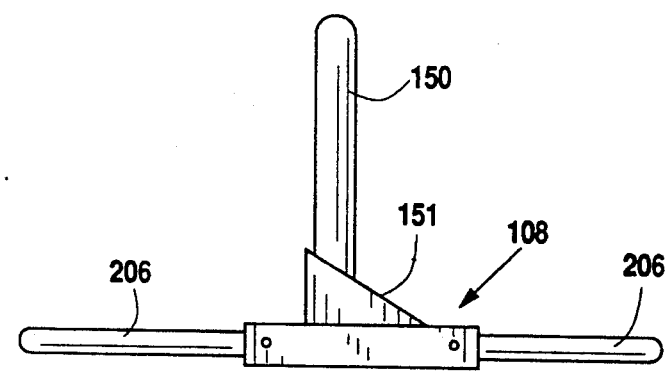
FIG. 12 is a side elevational view of the sliding pin plate of the apparatus of FIG. 2.
Figure 13:
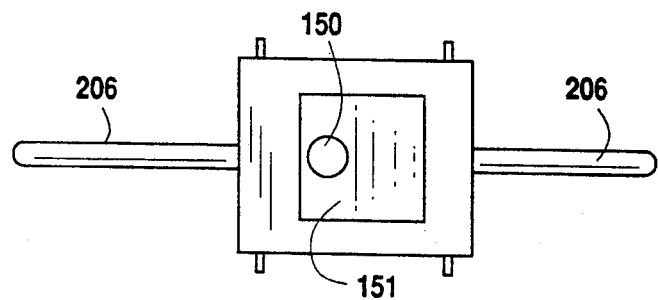
FIG. 13 is a top plane view of the sliding pin plate of FIG. 12 (the front surface).

Referring to FIGS. 12 and 13, pin sliding plate 108 exhibits a moving pin 150. Moving pin 150 serves to complete the configuration of a filament 21 for straight-line passage of the filament's needle end back through its turns and loops (as dictated jointly by the pins 132, 134, 136, 138, 140, 142, 144, and 146, and the ridges and recesses of middle plate 104 and front plate 102) after the filament 21 is threaded about and between pins 132, 134, 136, 138, 140, 142, 144, 146 in the hereinafter prescribed manner. A wedge 151 is centrally situated on the pin sliding plate 108 from which the moving pin 150 extends as depicted.

Figure 14:
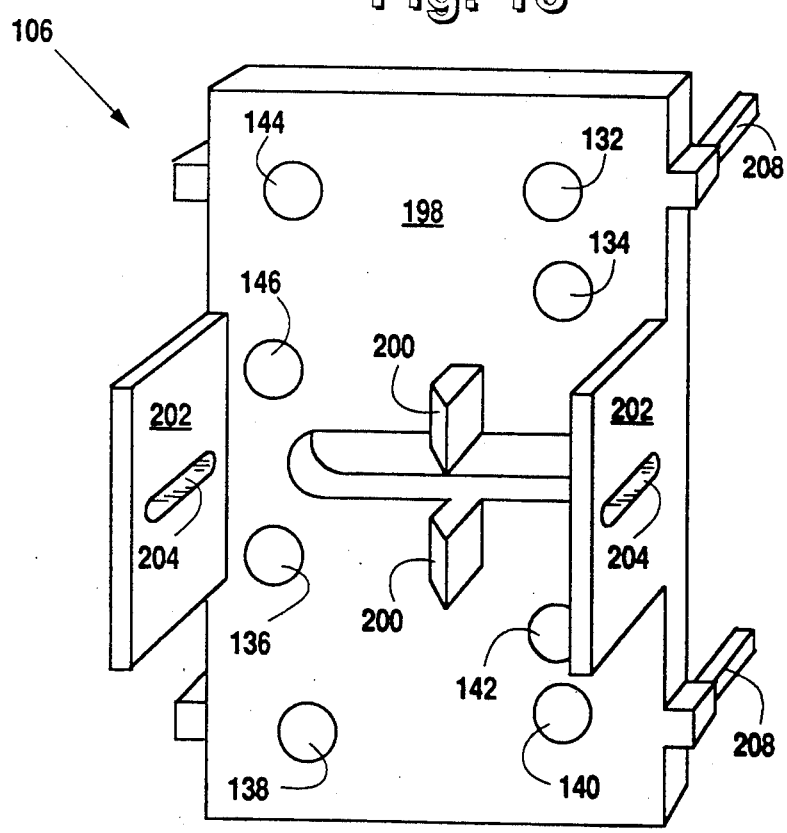
FIG. 14 is a perspective view of the back side of the pin plate of FIG. 10.

Referring in combination to FIGS. 12 and 14, the back face 198 of pin plate 106 exhibits two wedges 200. The outermost surfaces of the wedges 200 are flat and are oriented oblique to the back face 198 of the pin plate 106 at a complimentary angle to that of the front face of the wedge 151 of the pin sliding plate 108. Two track blocks 202 are situated on opposite sides of the back face 198 of the pin plate 106. Each track block 202 has a slot 204 oriented orthogonally to the exterior face 198. The slots 204 are for receiving rods 206 which extend from either side of the pin sliding plate 108. The interaction between the rods 206 and the slots 204, along with that between the wedge 151 and the wedges 200, serve to govern the movement of moving pin 150 within a desired range of movement.

Referring principally to FIGS. 5, 10 and 14, pin plate 106 exhibits four guide bars 208 which, by extending through guide blocks 210 on the middle plate 104, serve to stabilize the apparatus 100 and to allow the pins to be retracted and to allow the finished knot to be released.

Figure 15:
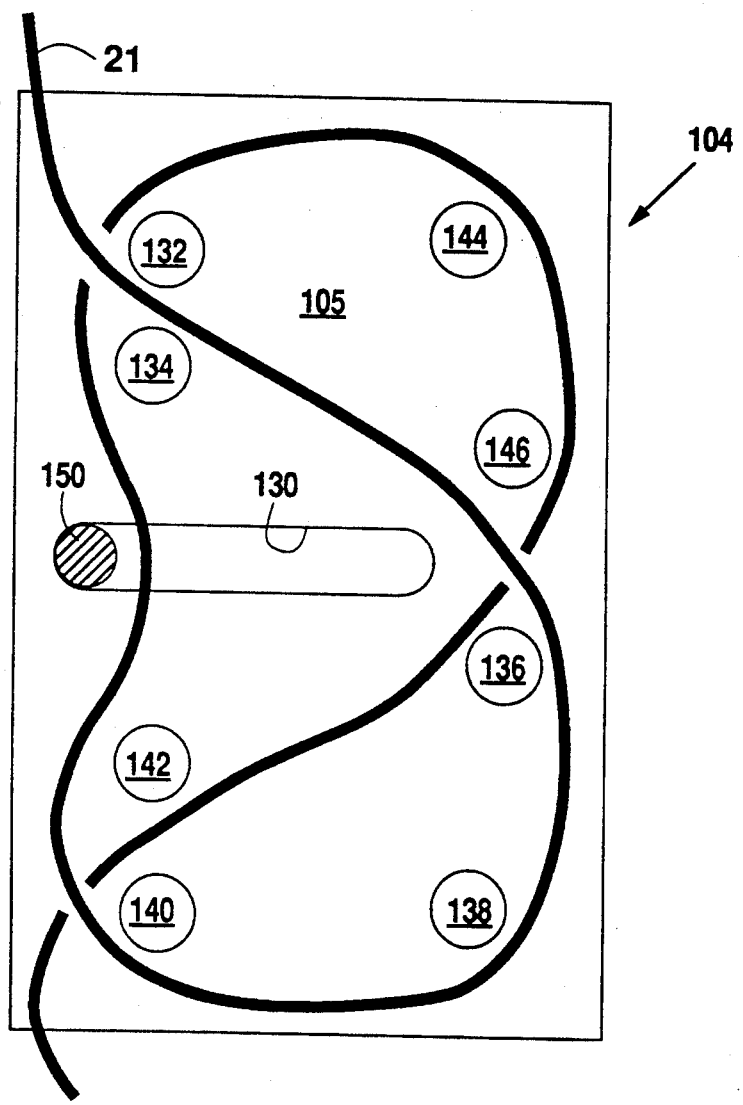
FIG. 15 is a schematic depiction of the arrangement of a filament on the front face of the middle plate of FIG. 15 when the filament is threaded about and between the apparatus's pins as herein disclosed and when the pin sliding plate is in the position depicted in FIG. 3.

Referring principally to FIG. 15, apparatus 100 should be initially configured such that the pins 132, 134, 136, 138, 140, 142, 144, 146 extend through the appropriate holes in the middle plate 104 as depicted. The pin sliding plate 108 should be moved to the position whereby moving pin 150 is retracted and, as when viewing FIG. 15 as depicted, positioned to the far left edge of slot 130. The top plate 102 should be hingedly opened.

With the apparatus 100 in the just-described configuration, a user should configure a filament 21 as shown in FIG. 15. To do so, the terminal end of filament 21 (that which is opposite the needle end 111) is immobilized generally at the bottom, left corner of plate 104. Holding the remainder of filament 21 in one's hand, the filament 21 is progressively lain on face 105 as follows: With directions corresponding to the depiction of FIG. 15, the filament 21 should first progress form the bottom left corner of plate 104, between pins 140 and 142, and, moving form left to right across face 105, toward pin 146. Filament 21 should next pass between pins 136 and 146 (contacting pin 146) and thereafter move in a counterclockwise progression outside of pins 144, 132, 134, 142, 140, 138 and 136 (in that order) insuring to pass to the inside of moving pin 150. Extending between pins 136 and 146 (contacting pin 136) the filament should finally be lain in a right to left progression across middle plate 104 to extend between pins 132 and 134 and beyond the upper right corner areas of the middle plate 104. The portion of filament 21 which extends beyond the upper right corner area of plate 104 is that which includes the needle end 111 and which will, in the final step of using apparatus 100, pass through the conclusion path to finally form a Capstan knot.

Once the filament 21 is configured on the middle plate 104 as just described, the top plate 102 is placed in position whereby pins 132, 134, 136, 138, 140, 142, 144, 146 extent into pin holes 160, 162, 166, 164, 152, 154, 158 and 156 respectively and front plate 102 and middle plate 104 are closely juxtaposed.

Figure 16A:
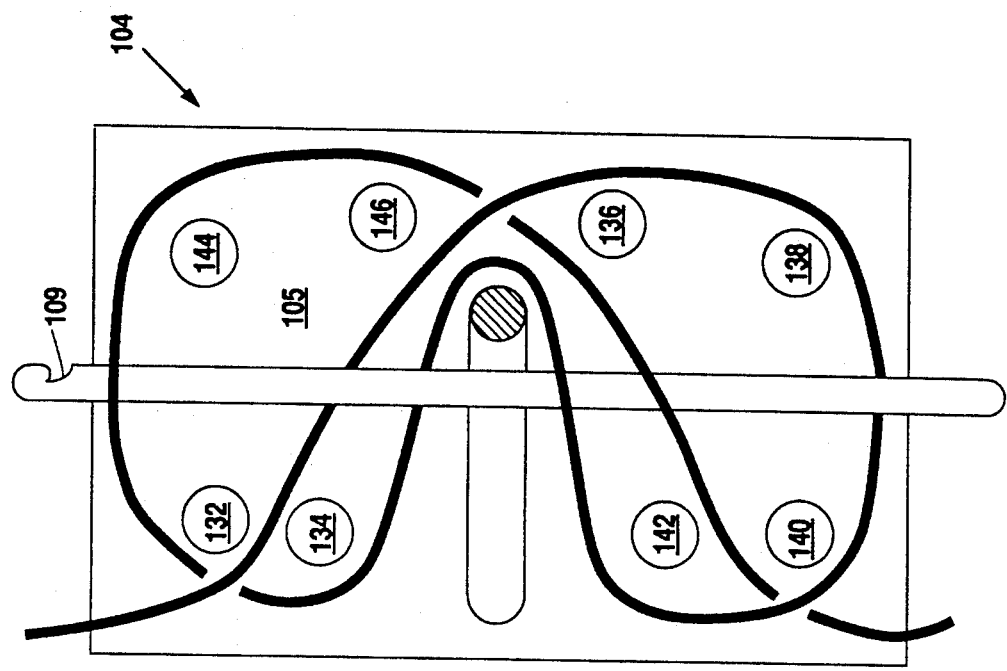
FIG. 16a is a schematic depiction of FIG. 16 with the latched needle (referenced number 109) in position.
Figure 16:
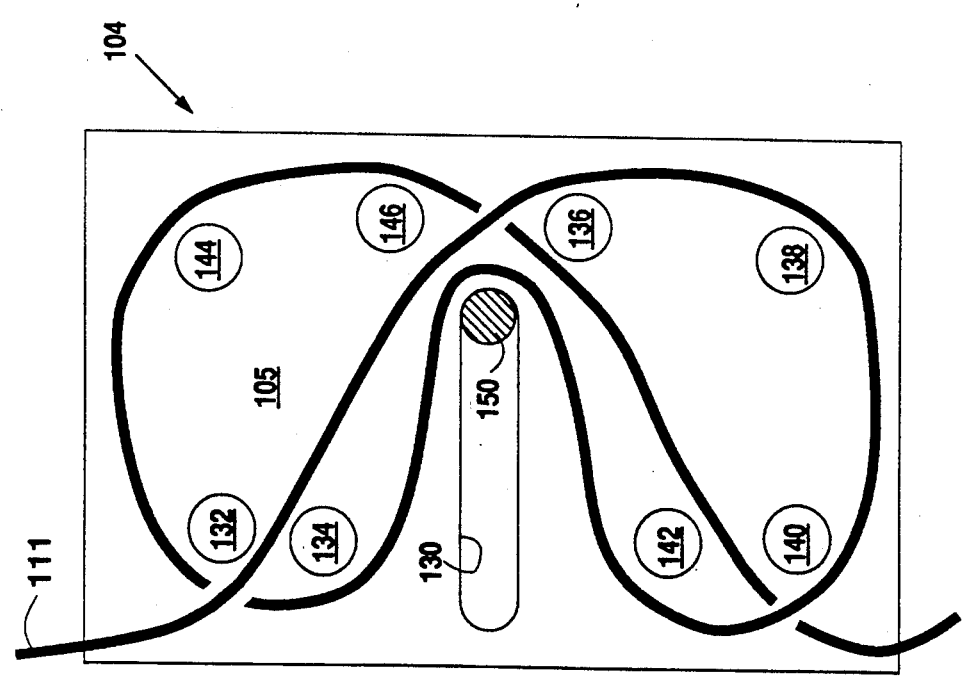
FIG. 16 is a schematic depiction of the arrangement of a filament on the front face of the middle plate of FIG. 15 when the filament is threaded about and between the apparatus's pins as herein disclosed and when the pin sliding plate is in the position depicted in FIG. 4.

The pin sliding plate 108 should next be moved to the other extreme of its permitted range of movement thereby repositioning the moving pin 150 and filament 21 as depicted in FIG. 16.

Figure 17:
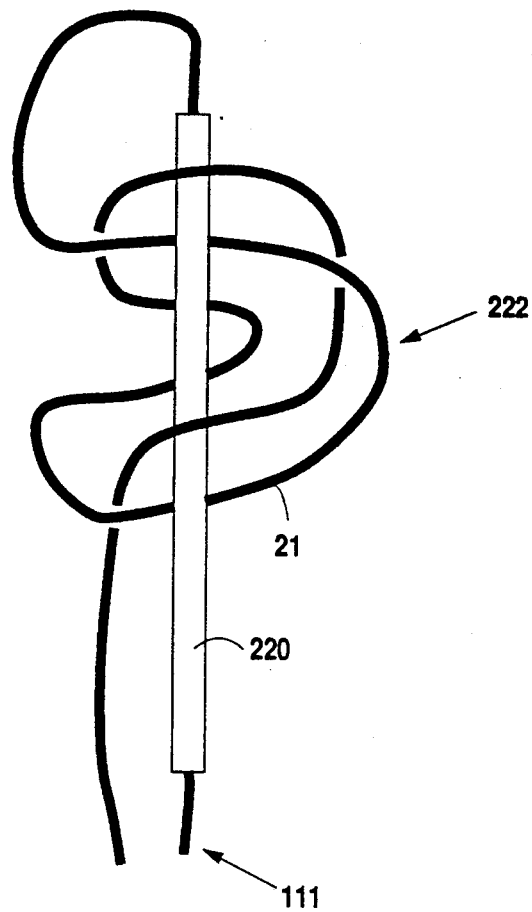
FIG. 17 is a depiction of the capstan knot as formed through use of a tube member and practicing a method as disclosed herein.
Figure 17A:
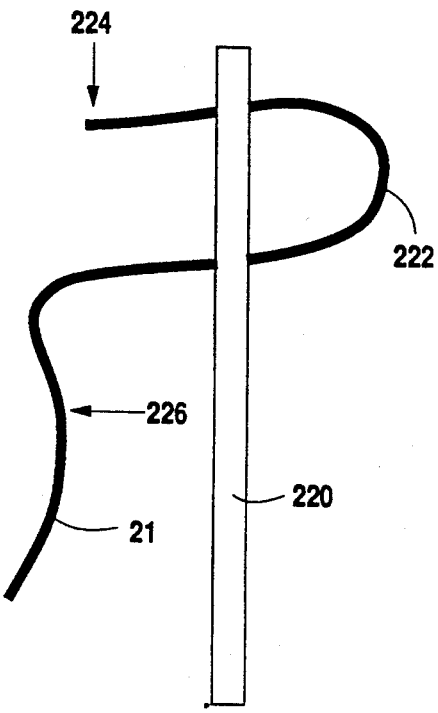
FIGS. 17a-d are serial representations of steps in the formation of a capstan knot using only a tubular member and the filament from which the knot is to be formed.
Figure 17B:
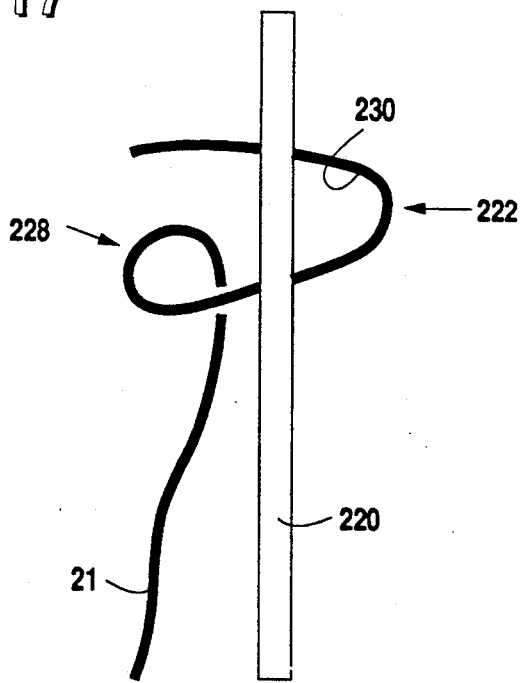
Figure 17C:
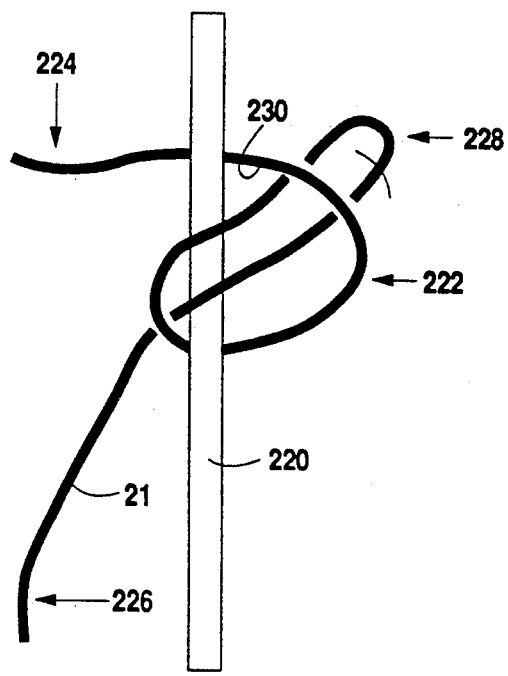
Figure 17D:
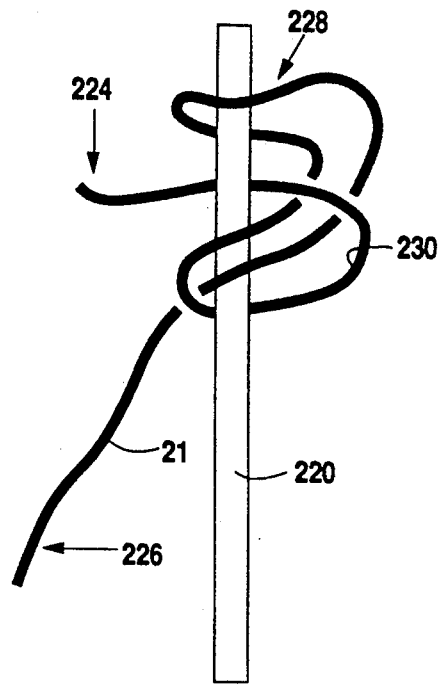

Referring in combination to FIGS. 1, 5, 9, 15, 16, 16a, and 17 it can now be appreciated how apparatus 100 initially forms the capstan protoknot and facilitates formation of the completed capstan knot 10. Most illustrative of this function may be a side-by-side comparison of FIGS. 5, 16a, and 17. FIG. 17 shows a loosely formed Capstan knot on a tube 220. It is clear that sliding the tube 220 from the end 111 of filament 21 would leave a Capstan knot which need only be tightened. Tube 220 in FIG. 17 should be understood to correspond to the conclusion path which is jointly defined by recesses 183 of plates 102 and 104. Turning to FIG. 16a, filament 21 is shown following substantially the same path in the horizontal plane as depicted in FIG. 17. To the extent that the appropriate segments of the filament 21, as threaded about the pins of apparatus 100 as above described, are held appropriately above or below the conclusion path before the needle end 111 of filament 21 traverses the conclusion path, then passing the needle end 111 of filament 21 through the conclusion path will necessarily form a Capstan knot. It is the cooperation of the opposing ridges and recesses of plates 102 and 104 which divert the filament 21 above and below the conclusion path so that passing the needle end 111 of filament 21 therethrough forms a Capstan knot. For example when plates 102 and 104 are juxtaposed with a filament 21 properly threaded therein, ridges 180 and 182 of plate 102 push a segment of filament 21 downward into recess 174 and below the conclusion path. This segment corresponds to that at the lowermost portion of FIG. 16a which is shown underlying the latched needle 109 and extends generally between pins 138 and 140. As the needle end 111 of filament 21 traverses the conclusion path, it will pass over this segment of filament 21 as affected by ridges 180 and 182 and recess 174.

Likewise, Ridges 188 and 190 of plate 104 serve to raise two segments of filament 21 relative to the conclusion path into recess 194 of plate 102. These segments correspond to the portions of Filament 21 in FIG. 16a which are shown overlying the latched needle 109 generally between pins 136 and 142 and to the lower side of the Figure from the moving pin 150. As the needle end 111 of filament 21 traverses the conclusion path, it will pass under these two segments of filament 21 as affected by ridges 188 and 190 and recess 194.

Figure 2:
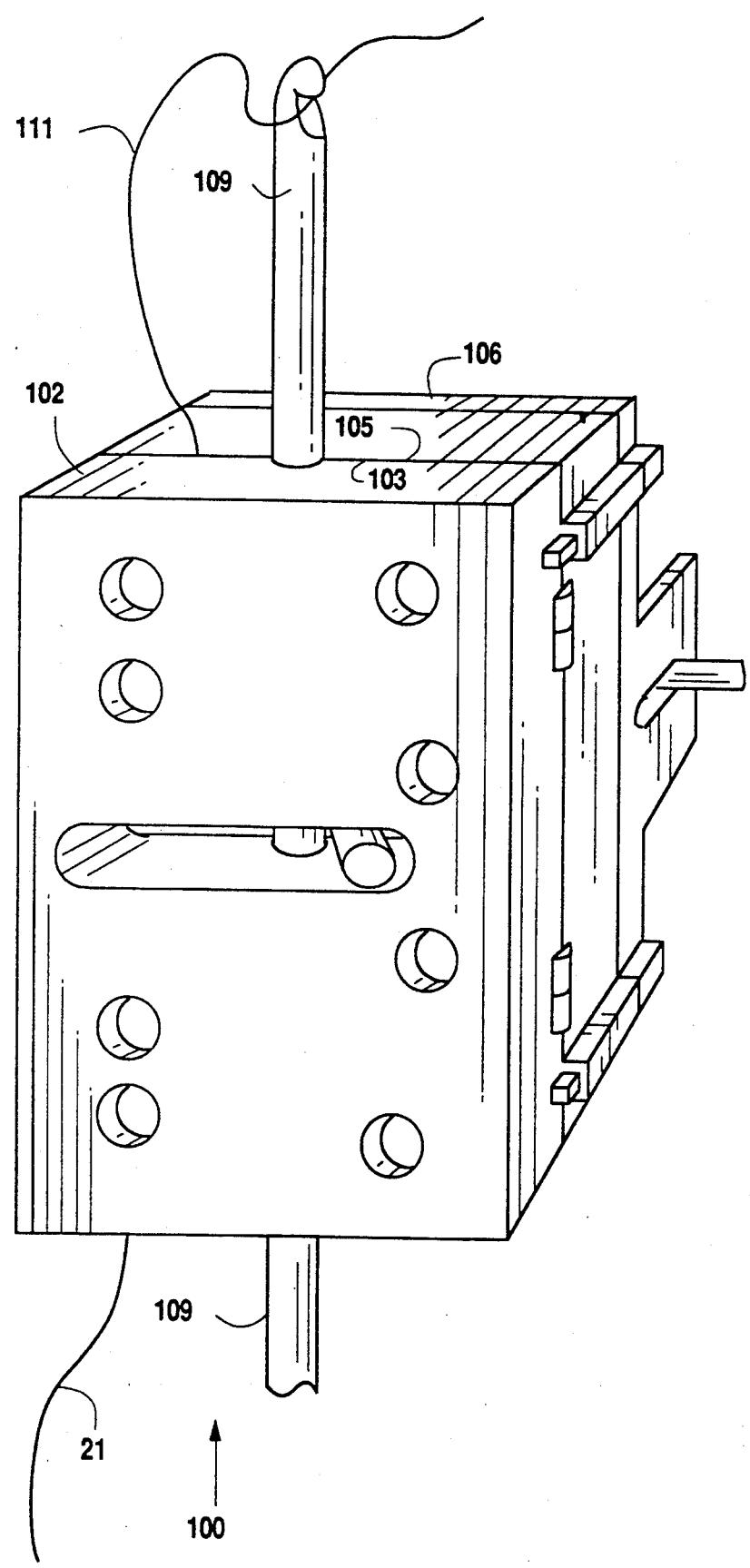
FIG. 2 is a perspective view of the knot tying apparatus as herein disclosed.

The other paired ridges and recess of plates 102 and 104 serve like functions to raise and lower appropriate segments of filament 21 relative to the conclusion path such that, upon passage of the needle end 111 of the filament 21 through the conclusion path, the configuration of the filament 21 as shown in FIG. 17 is substantially duplicated 109 (similar to a crochet needle and as depicted in FIGS. 2 and 16a) be used to draw the needle end 111 of filament 21 through the conclusion path defined by recesses 183.

As mentioned above, the capstan knot 10 can also be formed by following a procedure involving a tube member 220. Referring principally to FIGS. 17a-d, the following description of forming capstan knot 10 using tube member 220 will be made as if from the user's perspective looking straight forward at the filament 21 and tube member 220 in the user's hands.

With the tube member 220 in an upright orientation, double a length of filament 21 behind the tube member 220 such that a first filament bight 222 is formed to the user's right of the tube member 220, and the two lengths of filament 21 either side of the first filament bight 222 (the shorter terminal segment 224 and the longer needle segment 226) extend horizontally to the user's left of the tube member 220 with the terminal segment 224 of the filament 21 in the superior position and spaced approximately one inch from the needle segment 226 of the filament 21 which is in the inferior position.

Stabilizing this filament configuration against the tube member 220 with the right hand, the user should next grasp a segment of the needle segment 226 (to the left of the tube member 220) with the left thumb and index finger, the thumb being in the superior position and the index finger being in the inferior position, the user's wrist having been rotated to its fully counterclockwise extent prior to grasping the needle segment 226 and both digits extending away from the user.

The user next rotates his wrist in a clockwise direction thereby inverting the thumb and index finger and forming an over-hand loop in the needle segment 226 with the second filament bight 228 being held in between the left thumb and index finger. The user next moves the second filament bight 228 from left to right over the side of the tube member 220 nearest the user and passes the second filament bight 228, moving away from the user, through the space 230 defined by the first filament bight 222 and the right edge of the tube member 220.

While not further twisting the overhand loop of the needle segment 226, the user should next release it so as to grasp it on the distant most side of the first filament bight 222 (relative to the user). The user then passes the second filament bight 228, moving toward the user from the distant most side of the tube member 220, over the uppermost end 232 most side of the tube member 220. This completes formation of the protoknot of the capstan knot 10.

Figure 18:
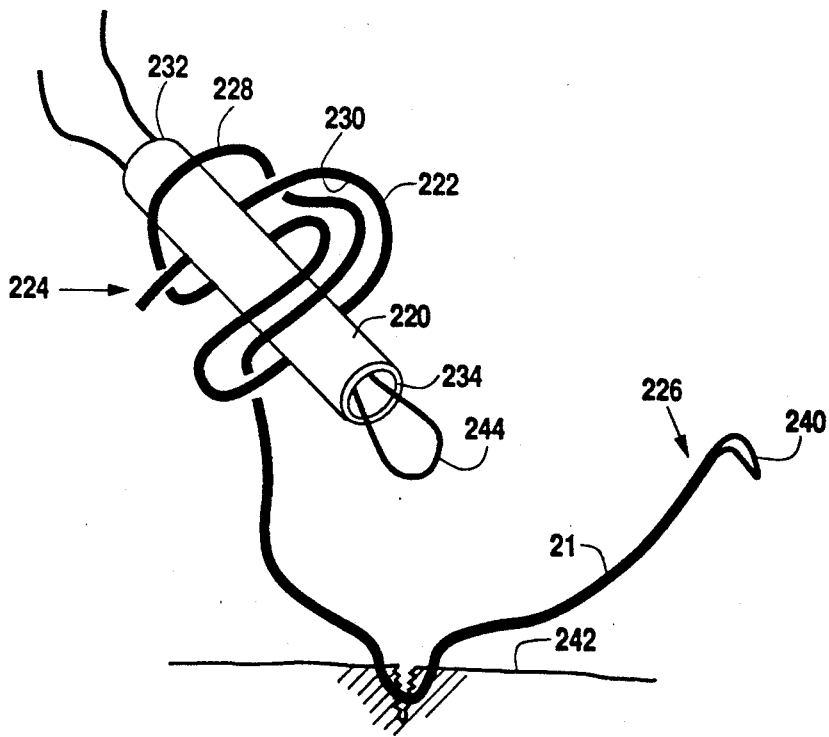
FIG. 18 is a depiction of a suture protoknot unit for formation of a capstan knot during a surgical procedure.

Referring principally to FIG. 18, after passage of the needle 240 through the to-be sutured tissue 242, the needle segment 226 of the filament 21 is drawn through the tube member 220 from the lower tube end 234 and exiting at the upper tube end 232 using the threading loop 244 thereby completing formation of the capstan knot 10. The tube member 220 is then removed from the filament 21 leaving the completely formed capstan knot 10 only to be suitably tightened adjacent the affected tissue 242.

It is expected that certain practitioners will prefer to form the capstan knot by the above-described tubular member-based methods. However, others who fully appreciate the utility and benefits of this knot in the surgical context may prefer that it be made available in the most easily used form possible.

In addressing the latter practitioners, Applicant suggests suture knot systems which include pre-formed suture protoknot units along with knot tighteners as are appropriate to the particular surgical procedure for which the system is intended (a more complete discussion of the knot tighteners disclosed by Applicant may be found in the above-referenced co-pending application by the present Applicant).

Referring again to FIG. 18, a pre-packaged capstan knot suture unit is suggested. With the filament 21 suitably immobilized relative to the tube member 220 through temporary affixation to a rigid platform (not shown in the drawing) such as sterilized fiberboard, a pre-formed protoknot for the capstan knot 10 may be marketed to the medical field. The filament 21 of such a unit would have a suture needle 240 affixed to the needle end 226 of the filament 21. The filament 21 would ideally be made available in a variety of suture materials and sizes.

As depicted in FIG. 18, use of such a unit would merely involve removing it from its packaging, passing the needle 240 through the patient's tissue 242 in appropriate relation to the incision to be closed, and then, using a threading loop 244 (supplied with the unit), drawing the needle end 226 of the filament 21 through the tube member 220 to complete the knot 10 as a suture. Thereafter only tightening the suture adjacent to the tissue 242 would remain.

Figure 21:
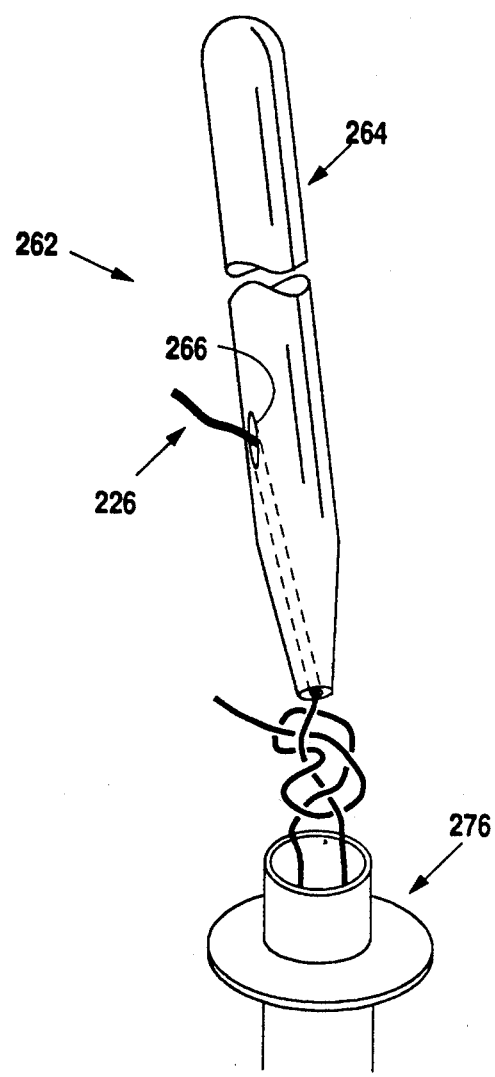
FIG. 21 is a view of a capstan knot slipped from the knot tightener of the pre-formed suture system of FIG. 19 with the suture filament extending into a canula which leads into a bodily cavity to the suture site (not shown).

Referring to FIGS. 1914 21, an alternative pre-formed suture system 262 would incorporate a knot tightener 264 which itself would serve as the tubular member such as tubular member 220 of FIG. 18. The knot tightener 264 exhibits a channel which passes through the tightener extending from the tightener tip 268 to a point on the shaft of the tightener 264 and being open at both ends. One making the pre-formed suture system 262 would use the tightener 264 in a manner analogous to that of using the tubular member 220 in tying the capstan knot as described above, Once the capstan protoknot is formed on the tightener 264, the protoknot should positioned on the shaft of the tightener 264 between its tip 268 and the opening 266 to the channel on the shaft of the tightener 264. In this manner, once the surgical needle 270 is passed through the patient's tissue 272, the needle 270 is cut and removed from the filament 21 and the needle end 226 of the filament 21 is passed through the channel moving from the channel opening at the tip 268 to the opening 266 on the shaft of the tightener 264. This corresponds to passing the needle end segment 226 of the filament 21 through the tubular member 220 as described above with reference to FIGS. 17.

To be practical for pre-packaging, the properly positioned capstan protoknot should be reversibly immobilized relative to the tightener 264 so that the protoknot does not slip from the tightener 264 prematurely. An easily removed, shrink-wrapped, medically acceptable plastic sheath about the protoknot (not shown in the drawings) would constitute one avenue for immobilization.

Figures 19, 20:
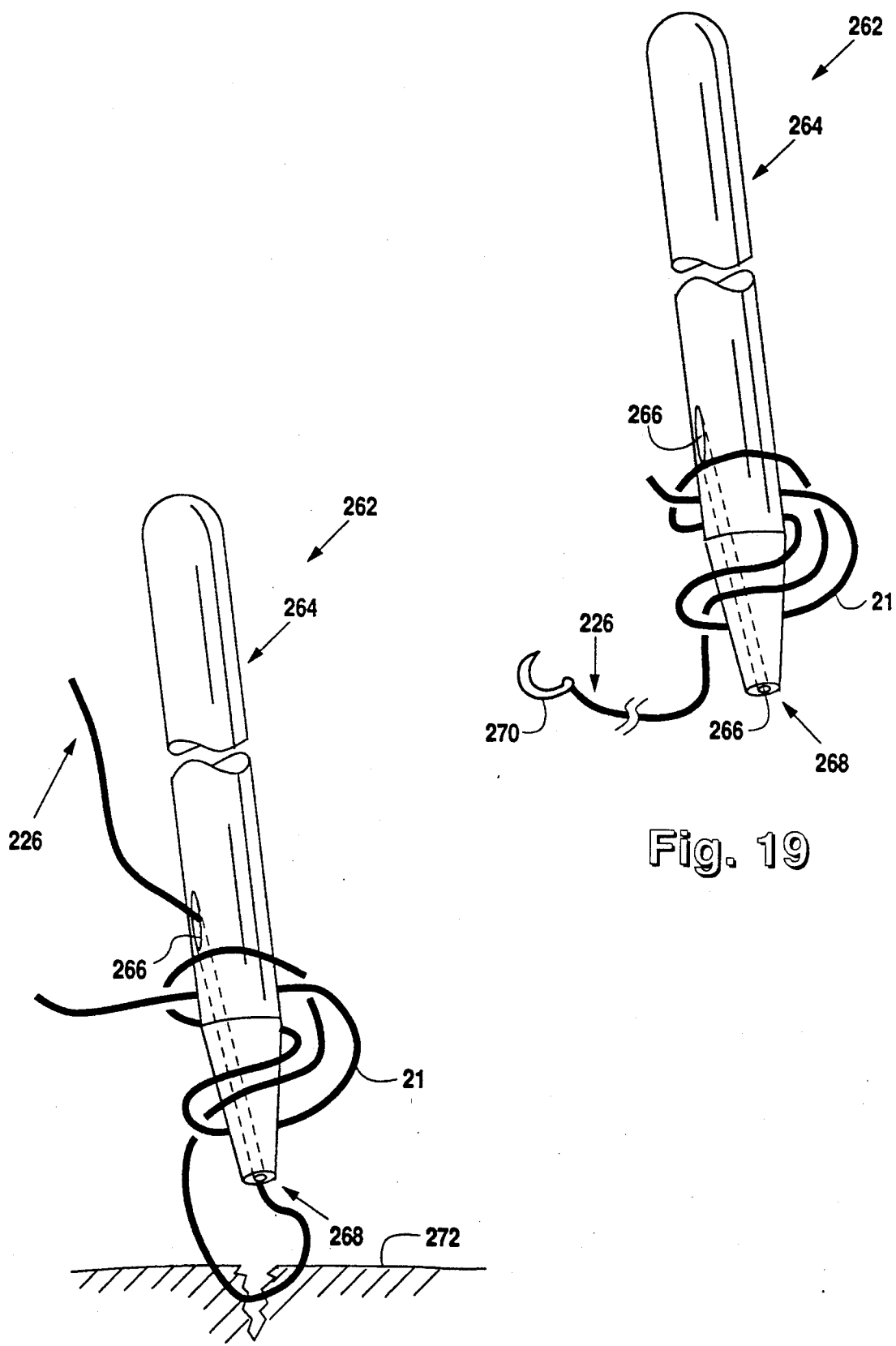
FIG. 19 is a depiction of a pre-formed suture system which incorporates a knot tightener and a pre-formed capstan protoknot (shown in loose formation and without packaging for ease of interpretation).
FIG. 20 is a view of FIG. 19 after removal of surgical needle and passage of needle end of filament through channel of tightener.

The pre-formed suture system 262 depicted in FIGS. 19-21 has extraordinary utility in surgical procedures involving limited access to the suture site. In order to use the capstan knot with its clear benefits, the surgeon need merely remove the system 262 from its outer packaging (not depicted in the drawings), pass the needle 270 through the affected tissue 272, thread the filament 21 (with the needle 270 removed) through the channel of the tightener 264, slide the tightener 264 from the filament 21 (as shown in FIG. 21), and set the knot with the tightener 264.

Referring specifically to FIG. 21, a canula 276 is shown in proximity to the pre-formed suture system 262 as in the case of endoscopic surgery where the suture knot is to be set well within a body cavity through an incision which make direct access impossible. It is in precisely such a situation where the pre-formed suture system 262 with the incorporated knot tightener 264 provides the greatest convenience, reliability and time savings. The knot, being in the nature of a slipknot, can simply be guided through the canula 276 by the knot tightener 264, and when in position "locked" by pulling the needle end of the filament 21 and pushing against the knot with the tightener 264 with equal and opposing force.

Figure 22:
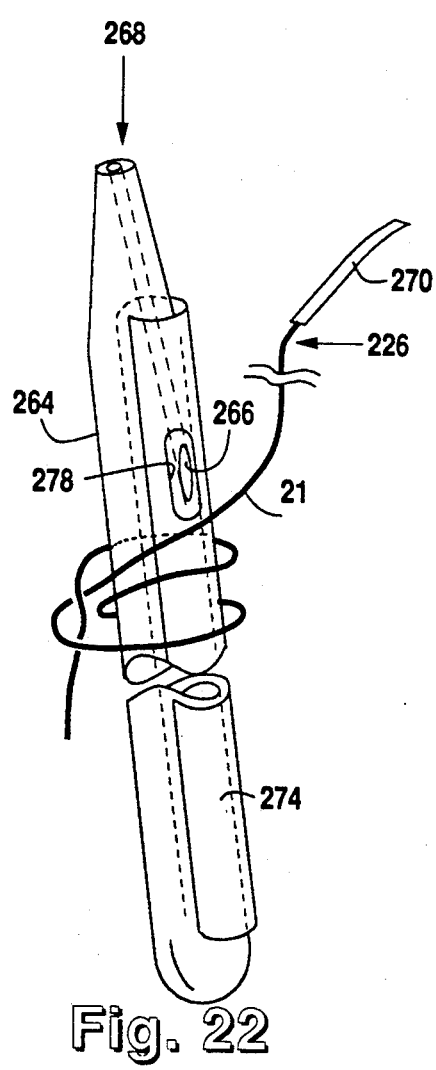
FIG. 22 is a perspective view of a pre-formed capstan protoknot suture system with a threading element associated therewith.
Figure 23:
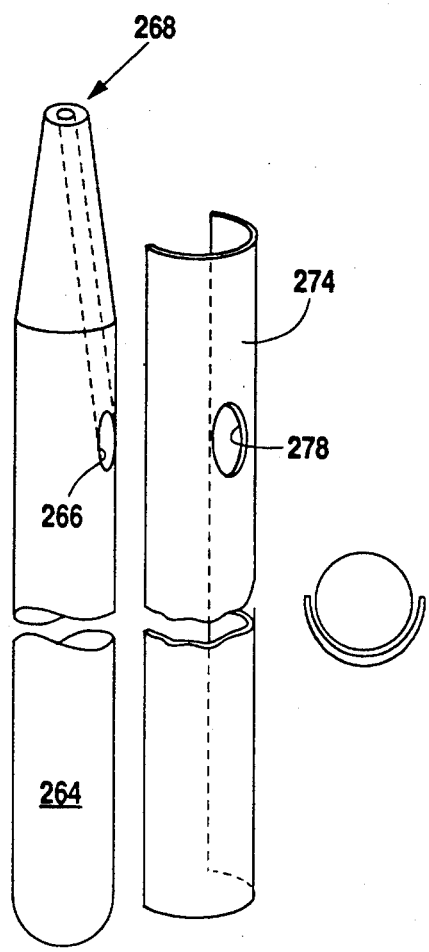
FIG. 23 is an exploded perspective of FIG. 22 with the suture filament removed from the drawing.

Referring to FIGS. 22 and 23, a still further improvement on the pre-formed suture system includes a threading member 274. The threading element 274 obviates the problems associated with having to form the capstan protoknot between the tip 268 of the knot tightener 264 and the hole 266 as shown in FIGS. 19-21. The threading member 274 is, in the preferred embodiment, a biased snap-fit member made from a suitably resilient plastic. Member 274 is sized to envelop approximately 220 radians of the 360 radian annular surface of the tightener 264. This arrangement insures a sufficiently secure snap-on engagement with the tightener 264, even when made to slide axially along the surface of the tightener 264.

The threading member 274 allows the protoknot to be positioned anywhere on the tightener 264. Once the filament 21 is passed through the patient's tissue 272 as above described, the needle 270 is removed and the filament 21 is thread through the channel of the tightener 264 and through the hole 278 of the threading member 274. A user then moves the threading member 274 axially along the tightener 246 in a direction opposite from the tip 268 so as to draw the filament 21 through the loops of the protoknot situated on the tightener 264 to complete formation of the (loosely formed) capstan knot. The tightener 264 is then used to position and tighten the knot as above described.

Figure 24:
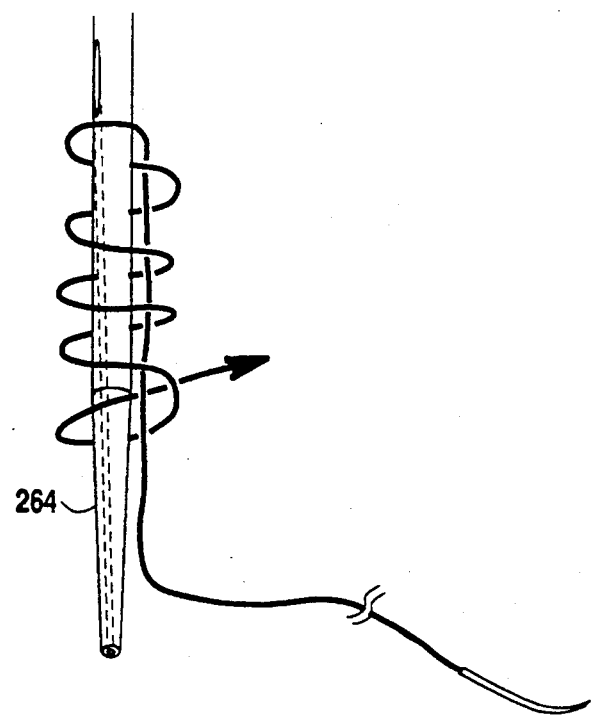
FIG. 24 depicts a Roeder loop formed on a knot tightener.

Finally, it should be noted that other slipknot protoknots may be situated on knot tighteners or tubular members so long as the protoknot can be transformed into a completed slipknot in a like manner as demonstrated above with reference to FIGS. 18-21. Examples of such others knots include, but are not necessarily limited to, the above-mentioned Roeder loop as depicted in FIG. 24.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention It is, therefore, contemplated that the appended claims will cover such modifications that fall within the scope of the invention.

I claim:

1. An apparatus for forming a capstan knot from a filament comprising:
   a sliding pin plate having a moving pin attached thereto and extending therefrom;
   a pin plate having a plurality of stationary pins extending therefrom; and
   a middle plate with a plurality of pin holes and a slot passing therethrough for respectively receiving said stationary pins and said moving pin therethrough, said stationary pins and said moving pin when extending through said middle plate together defining a first filament path on a middle plate interior face of said middle plate for threading said filament, said middle plate interior face having a first ridge, a first ridge receiving recess, and a elongate channel formed thereon, said first ridge and said first ridge receiving recess serving to orient said filament when threaded to traverse said first path whereby passing an end of said filament along said elongate channel completes formation of said capstan knot.

2. An apparatus for forming a knot from a filament comprising:

a plate having a plate interior face with a plurality of guide pins extending above said plate interior face, said guide pins for defining in first and second dimensions a first filament path on said plate interior face for a filament to traverse substantially in a first plane; said plate interior face further includes for defining said first filament path in a third dimension, first positioning means for diverting a first portion of said filament in a first direction substantially perpendicular to said first plane and second positioning means for diverting a second portion of said filament from said first plane generally in a second direction, substantially opposite said first direction; said plate interior face further exhibiting indicia which defines a second filament path by following which second filament path a needle segment of said filament threaded to traverse said first filament path completes formation of said knot.

3. The invention of claim 2 wherein said plate exhibits a moving guide pin slot, and wherein said apparatus further comprises:

a sliding pin plate having a moving guide pin extending therefrom which moving guide pin constitutes one of said guide pins when aid sliding pin plate and said plate are facially juxtaposed for said moving guide pin to extend through said moving guide pin slot, which moving guide pin, by extending through said plate, extends above said plate interior face; and a pin plate having a plurality of stationary guide pins extending therefrom, said stationary guide pins constituting all of said guide pins, except said moving guide pins, which extend above said plate interior face, said stationary guide pins extending through correspondingly positioned guide pin holes in said plate;

and further wherein said moving guide pin slot permits said moving guide pin to extend therethrough in a first heading and to move in a second heading, perpendicular to said first heading, for moving between first and second moving guide pin positions relative to said interior face of said plate; said first moving guide pin position being to facilitate threading said filament about said first filament path, and movement from said first moving guide pin position to said second moving guide pin position being for configuring said filament relative to said indicia for the formation of said capstan knot upon passage of said needle segment along said second filament path, said filament having first been threaded about said first filament path.

4. The invention of claim 3 wherein said positioning means comprise a plurality of first ridges and first recesses on said plate interior face for raising and lowering portions of said filament relative to said first plane.

5. The invention of claim 3 wherein said pin plate and said sliding pin plate are removable from said plate whereby said stationary guide pins and said moving guide pin may be withdrawn from said guide pin holes and said slot in said plate.

6. The invention of claim 2 wherein said positioning means comprise a plurality of first ridges and first recesses on said plate interior face for raising and lowering portions of said filament relative to said first plane.

7. The invention of claim 6 further comprising a top plate having a top plate interior face with a plurality of second ridges and second recesses, said second ridges and said second recesses being situated relative to each other on said top plate interior face whereby said first ridges may extend into said second recesses and said first recesses may receive said second ridges when said top plate interior face and said plate interior face are juxtaposed.

8. A method for forming a capstan knot comprising the steps of:

selecting a filament with a needle segment;
selecting an apparatus comprising:

a middle plate having a middle plate interior face with a plurality of guide pins extending above said middle plate interior face, said guide pins defining a first filament path on said traverse substantially in a first plane, said middle plate interior face further having positioning means for positioning said filament in directions substantially perpendicular to said first plane; said middle plate interior face further exhibiting indicia which defines a second filament path by following which second filament path the needle segment of said filament threaded to traverse said first filament path completes formation of said capstan knot;

threading said filament so as to traverse said first filament path; and passing said needle segment of said filament along said second filament path.

9. The invention of claim 8 wherein said apparatus further comprises:

a sliding pin plate having a moving guide pin attached thereto and extending therefrom which moving guide pin constitutes one of said guide pins which, by extending through a moving guide pin slot in said middle plate, extends above said middle plate interior face when said plate and said sliding pin plate are facially juxtaposed; and a pin plate having a plurality of stationary guide pins extending therefrom, said stationary guide pins constituting all of said guide pins, except said moving guide pin, which extend above said middle plate interior face, said stationary guide pins extending through correspondingly positioned guide pin holes in said middle plate;

and further wherein said moving guide pin slot permits said moving guide pin to extend therethrough in a first heading and to move in a second heading, perpendicular to said first heading, for moving between first and second moving guide pin positions relative to said interior face of said plate; said first moving guide pin position being to facilitate threading said filament about said first filament path, and movement from said first moving guide pin position to said second moving guide pin position being for configuring said filament relative to said indicia for the formation of said capstan knot upon passage of said needle segment along said second filament path, said filament having first been threaded about said first filament path.

10. The method of claim 9 wherein said positioning means comprise a plurality of first ridges and first recesses on said middle plate interior face for raising and lowering said filament relative to said first plane.

11. The invention of claim 10 wherein said apparatus further comprises a top plate having a top plate interior face with a plurality of second ridges and second recesses, said second ridges and said second recesses being situated relative to each other on said top plate interior face whereby said first ridges may extend into said second recesses and said first recesses may receive said second ridges when said top plate interior face and said middle plate interior face are juxtaposed.

12. The invention of claim 9 wherein said pin plate and said sliding pin plate are removable from said middle plate whereby said stationary guide pins and said moving guide pin may be withdrawn from said guide pin holes and said slot in said middle plate.

13. A method for forming a capstan knot comprising the steps of:

selecting a tubular member and a filament, said tubular member having a first and a second tube end;

with the long axis of said tubular member situated in a fixed reference orientation in a first plane (such as a vertical orientation relative to an individual forming said knot), doubling a length of said filament adjacent to said tubular member and on a first side of said tubular member (such as a side of said tubular member opposite from said individual) such that a first filament bight is formed at a first bight point situated on said first side of said tubular member and separated from said tubular member in substantially a first lateral direction from said tubular member, said first lateral direction being orthogonal to said fixed reference orientation (such as to the right of said tubular member from said individual's perspective) with a first terminal length of said filament and a second needle length of said filament extending from said first filament bight beyond and perpendicular to said tubular member in a second lateral direction orthogonal to said fixed reference orientation and substantially opposite said first lateral direction (such as behind said tubular member and toward the left thereof from said individual's perspective), said needle length and said terminal length lying substantially in a single second plane parallel with said first plane of said fixed reference orientation, said terminal segment lying closer to said first tube end than said needle segment and being separated from said needle segment by approximately one inch;

grasping a loop segment point a loop segment of said needle segment, said loop segment point lying substantially on said first side of and in said second lateral direction from said tubular member and twisting said loop segment approximately 180° (such as in a clockwise direction from said individual's perspective) so as to form a second filament bight which second filament bight delineates a first length of said needle segment from a second length of said needle segment, said first length of said needle segment being closer to said first filament bight than said second length of said needle segment, said twist being made whereby said second length of said needle segment intersects said first length of said needle segment such that, if such intersection were immediately adjacent to and contacting said tubular member on said first side of said tubular member, said first length of said needle segment would contact said tubular member and separate said second length of said needle segment from said tubular member;

moving said second filament bight substantially in said first lateral direction and across a second side of said tubular member, said second side being opposite said first side, so as to partially encircle said tubular member;

moving said second filament light in a third direction from said second side toward said first side of said tubular member and without further substantially twisting said loop segment, passing said second filament bight through a space the perimeter of which space is jointly defined by said first filament bight and said tubular member;

moving said second filament light in a fourth direction, substantially opposite from said third direction, from said first side of said tubular member toward said second side of said tubular member, passing said second filament bight around a section of said first filament bight closest said first tube end, and over said first tube end; and passing said needle segment of said filament through said tubular member moving from said second tube end to said first tube end.

* * * * *